United States Patent [19]

Sweedler et al.

[11] Patent Number: 5,141,609
[45] Date of Patent: Aug. 25, 1992

[54] METHOD AND DEVICE EMPLOYING TIME-DELAYED INTEGRATION FOR DETECTING SAMPLE COMPONENTS AFTER SEPARATION

[75] Inventors: Jonathan V. Sweedler, Redwood City; Jason B. Shear, Menlo Park; Richard N. Zare, Stanford, all of Calif.

[73] Assignee: The Trustees of the Leland Stanford Junior University, Stanford, Calif.

[21] Appl. No.: 614,830

[22] Filed: Nov. 16, 1990

[51] Int. Cl.$^5$ .............................................. G01N 27/26
[52] U.S. Cl. ........................... 204/180.1; 204/299 R; 356/344; 210/198.2; 210/656; 73/61.52
[58] Field of Search ..................... 204/180.1, 299 R; 356/344; 210/198.2, 656; 73/61.1 C

[56] References Cited

U.S. PATENT DOCUMENTS

| | | | |
|---|---|---|---|
| 4,559,695 | 12/1985 | Baker | 204/192.34 |
| 4,874,492 | 10/1989 | MacKay | 204/299 R |
| 4,904,366 | 2/1990 | Tokita | 204/299 R |

OTHER PUBLICATIONS

Cheng et al., "Charge-Coupled Device Fluorescence Detection for Capillary-Zone Electrophoresis (CCD-CZE)", *Applied Spectroscopy*, vol. 44, No. 5, (1990), pp. 755-765.

*Primary Examiner*—John Niebling
*Assistant Examiner*—Caroline Koestner
*Attorney, Agent, or Firm*—Majestic, Parsons, Siebert & Hsue

[57] ABSTRACT

This invention relates to a detection method and apparatus useful in capillary electrophoresis and capillary chromatography that employs an array of solid state detector such as a charge-coupled device operating in the time-delayed integration mode which allows more exposure time of the moving analyte zones. The CCD is synchronized so that after a normal exposure of the CCD, the charge information in every row of the CCD is shifted toward one end of the CCD and the charge/signal information in the last row is quantified. Applying the CCD and the time-delayed integration method in effect increases the effective sampling volume of the flow cell without introducing band broadening. Use of the CCD as a fluorescence detection in capillary electrophoresis separations allows analytes to be differentiated both in migration time and fluorescence emission, yielding detection limits for fluorophores in the $1-8 \times 10^{-20}$ mole range.

40 Claims, 5 Drawing Sheets

METHOD AND DEVICE EMPLOYING TIME-DELAYED INTEGRATION FOR DETECTING SAMPLE COMPONENTS AFTER SEPARATION

The government has rights to the invention pursuant to a NSF Grant CHE-8907446 and National Institute of Mental Health Grant Number MH45423.

FIELD OF THE INVENTION

The invention relates generally to a method and apparatus for detecting analyte bands and more particularly to a method and apparatus for time-delayed integration with a solid-state detector such as a charge-coupled device in capillary electrophoresis and capillary chromatography, or other sample separation techniques.

BACKGROUND OF THE INVENTION

Numerous research areas in biochemistry depend on the ability to analyze minute quantities of nucleic acids, amino acids, and peptides, yet many present detection schemes have inadequate sensitivity. Examples are the analyses of single cells and subcellular compartments. One of the few techniques to permit successful assays of the contents of a single cell is capillary zone electrophoresis (CZE), a powerful separation technique for the analysis of small sample volumes. Olefirowicz, T. M.; Ewing, A. G., Anal. Chem., 1990, 62, 1872–1876; Wallingford, R. A.; Ewing, A. G., Anal. Chem., 1988, 60, 1972–1975; Chien J. B.; Wallingford, R. A.; Ewing, A. G., J. Neurochem., 1990, 54, 633–638; and Kennedy, R. T.; Oates, M. D.; Cooper, B. R.; Nickerson, B.; Jorgenson, J. W., Science, 1989, 246, 57–63. Separation efficiencies routinely exceed several hundred thousand theoretical plates, and typical injection volumes are 10 nL or less.

For CZE, channel diameters usually range from 25 to 100 microns; therefore, designing methods to detect low concentrations in these small capillaries is a challenge. Laser-induced fluorescence (LIF) is currently the most sensitive detection method for CZE; detection limits are in the low attomole range. Nickerson, B.; Jorgenson, J. W., , J. High Resolut. Chromatogr. Commun., 1988, 11, 533–534; Drossman, H.; Luckey, J. A.; Kastichka, A. J.; D'Cunhan, J.; Smith, L. M., Anal. Chem., 1990, 62, 900–903; and Kuhr, W. G.; and Yeung, E. S., Anal. Chem., 1988, 60, 2642–2646. In these systems, the capillary is used as the flow cell, the laser illumination is perpendicular to the capillary, and a photomultiplier tube (PMT) monitors the fluorescence. Dovichi and coworkers developed a more sensitive method that has the same excitation geometry but uses a sheath flow cuvette as the sample cell and thereby eliminates much of the scattered light and luminescence from the fused silica capillary. With this technique, detection limits in the low zeptomole range ($10^{-21}$ moles) for fluorescently tagged amino acids have been reported. Cheng, Y.-F.; Dovichi, N. J.; Science, 1988, 242, 562–564; Wu, S.; Dovichi, N. J.; J. Chromatogr., 1989, 480, 141–155; Dovichi, N. J.; and Cheng, Y.-F., Am. Biotechnol. Lab., 1989, 7, 10–14.

However, despite the above advances in detection techniques, there remains a need for detection methods and devices with greater sensitivity.

SUMMARY OF THE INVENTION

Higher detection sensitivity and other objects are accomplished by the present invention where components separated from a sample as migrating analyte bands are detected by use of an array of solid state detectors. Each detector is capable of collecting radiation signals to produce charges. The sample is separated by conventional means, including capillary electrophoresis and capillary chromatography, in which the separated analyte bands migrate in a detector zone. Thereafter, means are employed to generate radiation signals that are indicative of said bands in the zone. Conventional means including ultraviolet absorption, fluorescence, phosphorescence, or chemiluminescence can be employed to generate the signals. The array of solid state detectors are correlated with the detection zone along the migrating direction of the bands so that as each analyte band migrates through the detector zone the radiation signals indicative of said band are directed to each detector in sequence. The solid state detector array is also designed so that the charges from each detector is shifted to the respective adjacent detector in the direction of the migration at a rate that is synchronized to the movement of the analyte band thus permitting the charges corresponding to the radiation signals of an analyte band to be accumulated at an array output.

The array could be one or two dimensional. In a two-dimensional array where each row of detectors consists of multiple detector elements, the intensities at a range of wavelengths of the radiation signals can be measured. In a one dimensional array where each row consists of a single element, the intensity measured is the sum of the intensities at different wavelengths in the range.

In a preferred embodiment, a charge-coupled device (CCD) is employed in a fluorescence detection system. Analyte bands separated by capillary zone electrophoresis are detected in a small section of an axially illuminated capillary column. The CCD is operated in the time-delayed integration (TDI) mode that allows long exposure times of the analyte zone. In the TDI mode, the transfer of the photogenerated charge in each row of the CCD proceeds approximately at the same rate as the migration of the solute bands in the capillary. Hence, as each analyte band enters the laser excitation zone, the fluorescence is collected and focused onto the first row of the CCD. After an appropriate time period, the charge in the CCD is shifted toward the readout register by one row. This time interval corresponds approximately to the time required by the band to move in the capillary by a distance so that the same analyte fluorescence signal causes an additional charge to be produced in the second row of the CCD, during the next time period, where this additional charge is accumulated and added to the charges shifted from the first row. The charge shifting is then performed for subsequent time intervals in the same manner at a rate synchronized with the movement of the band until the band exits the detection zone. At the same time, the total charge thus accumulated will be shifted to the array output. The effective integration time for a given analyte band is thus the entire time the band is within a window in the illuminated area; however, multiple bands can be within the illumination window simultaneously and still be resolved because of their different spatial positions. The time-delayed integration method in effect increases the effective sampling volume of the flow cell without introducing band broadening.

DETAILED DESCRIPTION OF THE PREFERRED EMBODIMENTS

General Description. The present invention encompasses a method and apparatus employing time-delayed integration for detecting components separated from a sample. The invention employs an array of solid state detectors to respond to radiation signals indicative of said components. Conventional means including ultraviolet absorption, fluorescence, phosphorescence, or chemiluminescence can be employed to generate the signals. Separation techniques that can be employed are any that can separate sample components into discrete units moving within a confined region, said region to be referred as the observation or detection zone. For instance, capillary electrophoresis, capillary chromatography, or micellar electrokinetic chromatography could be employed. Moreover, a portion of the capillary where the separated analyte bands traverse that is transparent to the radiation of interest could be used as the detection zone where the radiation signals are collected. With CZE, for example, once the sample is separated into migrating analyte bands they are detected by the array of solid state detectors, where each detector is capable of collecting radiation signals to produce charges. The array of solid state detectors are aligned with the detection zone along the migrating direction of the bands so that as each analyte band migrates through the detector zone the radiation signals indicative of said band are directed to each detector in sequence. The solid state detector array is also designed so that the charges from each detector is shifted to the respective adjacent detector in the direction of the migration at a rate that is synchronized to the movement of the analyte band such that the charges corresponding to the radiation signals of a particular analyte band can be accumulated at an array output.

The array could be one or two dimensional. In a two-dimensional array where each row of detector consists of multiple detector elements, both the intensity and wavelength characteristics of the radiation signals can be measured. In a one dimensional array where each row consists of a single element the measured intensity is normally the sum of the intensities measured at different wavelengths.

Charge-Coupled Device. A solid state device comprising an array of detectors which can be readily adapted for use in the present invention is the charge-coupled device (CCD). A CCD is a monolithic large-format silicon array detector. Characteristics that make it ideally suited for detection are extremely high quantum efficiency ($\leq 80\%$), virtually no dark current, and up to $10^6$ individual detector elements in the array. The CCD is conceptually similar to an electronic photographic film in that both integrate signal information. The integrating ability of the CCD and lack of dark current allow the CCD to perform exceptionally well in situations where several seconds are allowed for integration of the signal. In microcolumn separations, detection zones can be constructed such that analyte bands are viewed for many seconds—an ideal measurement task for a CCD.

As is described below, the two-dimensional nature of the CCD allows a detection scheme known as time-delayed integration to be used to increase even further the sensitivity, selectivity, and utility of CZE. After a normal exposure of the CCD, the charge information in every row of the CCD is shifted toward one end of the detector and the charge/signal information in the last row is quantified. Thus, the photogenerated charge originally created in a particular row of the CCD is transferred in a step-wise fashion toward the readout register.

Normally, the transfer of charge is started after an exposure and continues until the entire CCD has been read. In the time-delayed integration mode, the transfer of each row of the CCD proceeds approximately at the same rate as the migration of the solute bands in the capillary. Hence, for instance, in LIF, as the analyte band enters the laser excitation zone, the fluorescence is collected and illuminates the first row of the CCD. After the appropriate delay, the charge in the CCD is shifted toward the readout register by one row at approximately the same time as the band has moved down the capillary so that the analyte fluorescence signal is still contributing to the same charge information. The effective integration time for a given analyte band is the entire time the band is within the illuminated area; however, multiple bands can be within the illumination window simultaneously and still be resolved because of their different spatial positions aligned to different rows of detectors. The TDI method in effect increases the effective sampling volume of the flow cell without introducing band broadening. The effective increase in either sampling volume or integration time (two aspects of very closely related parameters) is a function of the number of rows of the CCD. With the availability of 512 by 512 element and larger CCDs, the TDI mode results in large increases in sensitivity.

The synchronization of the shift rate to the analyte velocity needs to be fairly accurate or a loss in separation efficiency is observed. Fortunately, the shift rate synchronization is not difficult. Because the start of the CZE run is known exactly, as is the distance from the injector to the center of the observation zone, the shift rate is determined by several geometrical parameters.

The invention will be described herein using a LIF/CZE system but the invention is applicable to capillary chromatography as well. Moreover, the invention is applicable to radiation detection techniques in general including, for instance, absorption, fluorescence, phosphorescence, and chemiluminescence, or the emission of high energy radiation (e.g., radioactive decay).

The LIF/CZE system uses a two-dimensional CCD containing an array of 516 by 516 detector elements. CCDs are available in arrays ranging from 64 by 64 to more than 2048 by 2048 elements. The system employs an unique axial illumination arrangement for CZE that has several advantages when used with multichannel detectors. The output of a laser is focused into the end of the capillary, the fluorescence emission from the analyte is collected over a 2 cm section of the channel, and the entire fluorescence spectrum is measured using the CCD array. In this way, the fluorescence cell is on-column, and the complete fluorescence spectrum is acquired simultaneously. Residence times for analytes in the 2 cm detection or observation zone range from 2 to 45 s. The axial illumination method allows the CCD to be operated in the snapshot and TDI modes and provides significant advantages over conventional illumination and CCD detection.

Time-Delayed Integration Mode. The TDI readout mode is ideally suited to LIF/CZE with axial illumination, in which the analyte band passes through an extended detection zone. Using this technique, the CCD becomes a highly sensitive and flexible multichannel fluorescence detection system. TDI, which does not use a shutter as in the snapshot mode, can acquire entire spectra at a 50 ms rate, and can spatially resolve multiple bands that are in the observation zone. Furthermore, far less data are generated than in the snapshot mode.

Description of CCD Operation. In a CCD, all the photogenerated charge in the photoactive elements is transferred toward the serial register one row at a time, and the charge information in the serial row is read using the single on-chip amplifier. Sweedler, J. V.; Billhorn, R. B.; Epperson, P. M.; Sims, G. R.; Denton, M. B.; Anal Chem., 1988, 60, 282A-291A. For a 516 by 516 element CCD, each time a single imaging area is transferred to the serial register, 516 readouts are performed; each readout corresponds to a different spectral element. This process continues until all 516 rows have been read 516 times.

Figure 1:
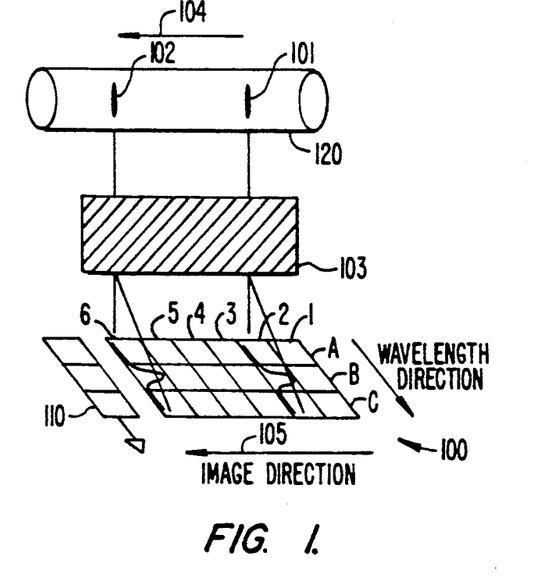
FIG. 1 is a schematic diagram of the CCD/LIF system illustrating the time-delayed integration mode.
Figure 3:
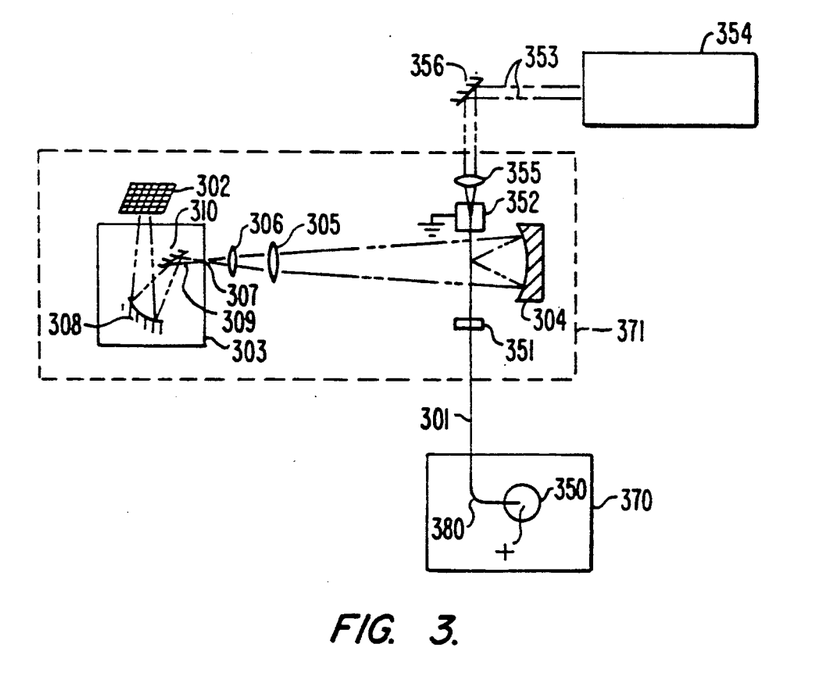
FIG. 3 is a schematic diagram showing the Ar ion laser, capillary arrangement, optics, and CCD detector.
Figure 7:
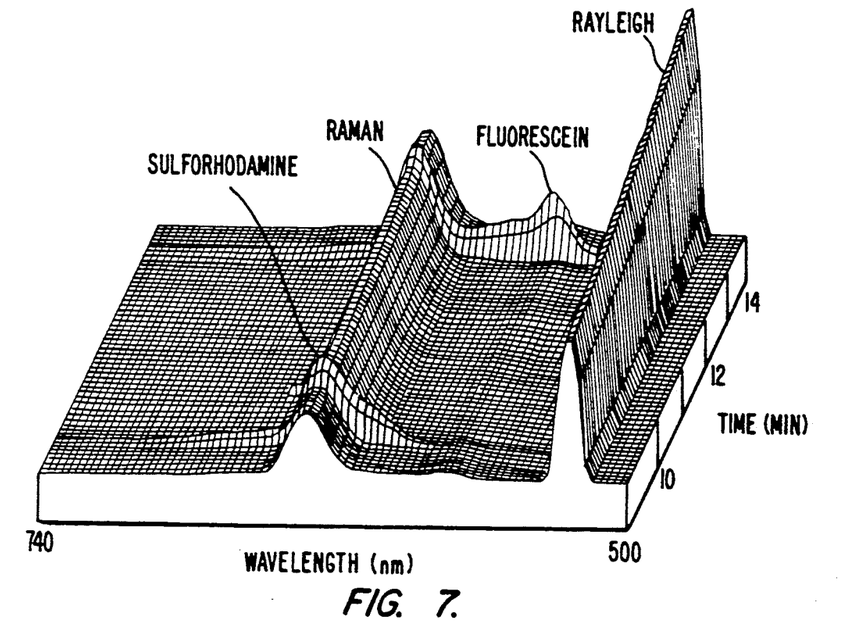
FIG. 7 is a TDI electropherogram of sulforhodamine and fluorescein.

Normally these transfers are done with a closed shutter to prevent exposure of the CCD to the illumination source; if such exposure occurs, the image becomes blurred. With the present invention the shutter is eliminated and in the CCD the shifting of rows is synchronized to the migration rate of the analyte band in the capillary. FIG. 1 illustrates the TDI mode using a simplified 3 by 6 element CCD and two separated analyte bands 101 and 102 that are migrating in detection or observation zone 120 of a capillary. The detection zone (or illumination window) is that portion of the capillary where the radiation signals (which is light in the embodiment of FIG. 1) indicative of the analtye bands are collected and directed to the CCD. As is apparent from FIG. 1, while the length of the detector zone may be the same as the length of the CCD array, it will be understood (as shown in FIG. 3) that they may be different, since light passing through the band or originating therefrom may be directed by optical means to the rows of the CCD. CCD 100 has a serial readout register 110 and six rows of photoactive elements denoted 1, 2, 3, 4, 5, and 6, respectively. Each row contains three photoactive elements. In FIG. 1, each row is perpendicular to the band motion; however, the rows need only be transverse to band motion direction 104 to practice the invention. The CCD is oriented so that the parallel shift direction 105 is the same as the direction of analyte band motion 104. As an analyte band enters the laser excitation zone, the fluorescence through the proper optics and spectrograph (collectively represented as element 103) is collected and illuminated onto row 1 of the CCD. The image that is projected onto each row of the two-dimensional CCD is a spectrum that is representative of the particular analyte band. As shown in FIG. 1, each row has three detector elements that are designated A, B, and C, respectively. Thus in this two-dimensional array, the image focused onto elements A, B, and C, respectively, would be from different portions of the spectrum of the light passing through or originating from the analyte band. As is apparent, by increasing the number of detector elements per row in a CCD one can measure radiation over a larger band of wavelengths. When an image is focused onto a detector element, the element generates a charge. Meanwhile, the band takes a period of time to migrate to the point on the capillary from which its image is projected onto CCD row 2. This is shown in FIG. 1 by the image from analyte band 101 that is focused onto row 2. Once the image of the band reaches row 2, each detector element therein will generate a charge. As the image of the analyte band moves from row 1 to row 2, the charge from row 1 is also shifted to row 2. Specifically, any charge generated in element A of row 1 is shifted to element A of row 2, any charge generated in element B of row 2 is shifted to element B of row 2, and so on. The shifting permits the charges to be accumulated so that when, for instance, the image is focused onto row 2, the charge generated by row 2 will be added to the charge shifted from row 1. This synchronized accumulation and shifting of charge continues step-wise over each pair of adjacent rows of the detector array over six consecutive time intervals until all the charges produced by all six rows 1-6 have been accumulated and shifted in the manner described in row 6, where upon the charges are read by means of read out register 110. In this fashion, the light signals from a particular band contribute to the same charge information which is read at the serial readout register of the CCD. An electropherogram illustrating the measured intensities over a wavelength range for different analytes is shown in FIG. 7 which is described below. The effective integration time for a given analyte band is the entire time the band is in the detection zone; however, multiple bands can be within this zone simultaneously and still be resolved because of their different spatial positions.

Figure 2A:
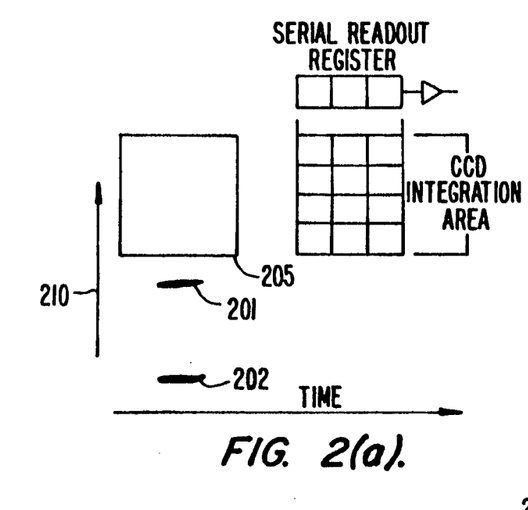
FIGS. 2(a) through 2(e) are another illustration of the CCD/LIF system.
Figure 2B:
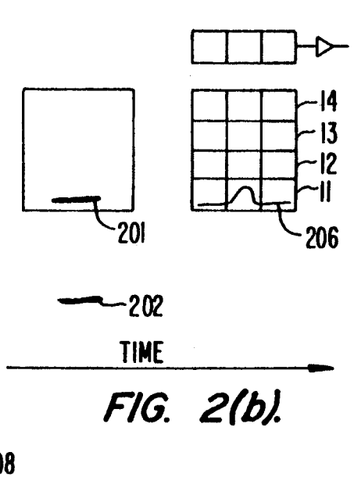
Figure 2C:
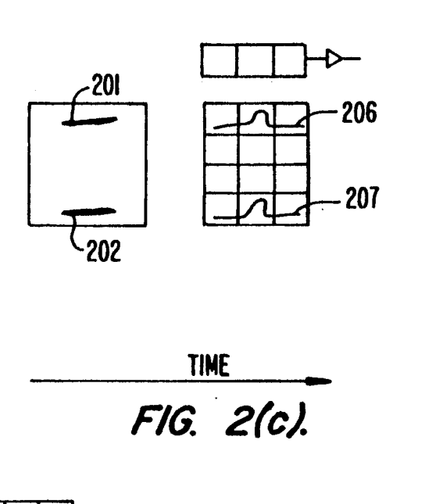
Figure 2D:
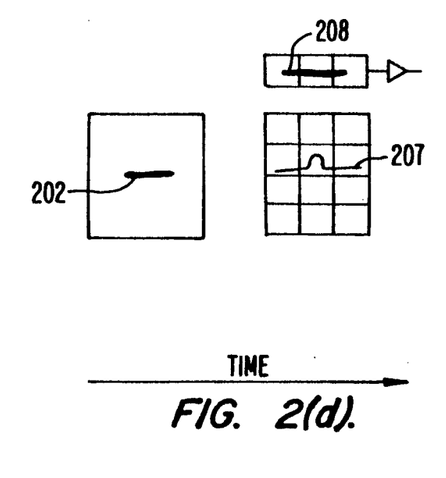
Figure 2E:
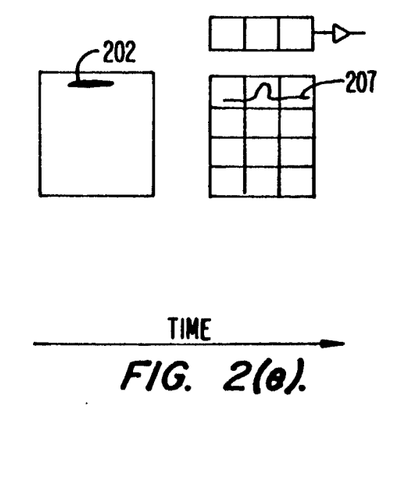

FIG. 2(a)-(e) is another illustration of the TDI method using a 3 by 4 element CCD. Here the four rows are designated 11, 12, 13, and 14, respectively. As each of the two analyte bands 201 and 202 migrates across the detection zone 205 of the capillary (not shown) in direction 210, its spectrum is focused onto the CCD integration area beginning at row 11. In FIG. 2(a), neither ban has entered the detection zone, but in FIG. 2(b), band 201 is in the zone. As shown on FIG. 2(b), the spectrum 206 of the analyte band 201 illuminates all three detector elements of row 11. Thus, with a two-dimensional solid state array like a CCD, the invention also permits intensity measurements at different wavelengths. If a one-dimensional array is used, the intensity over a band of wavelengths would be detected. As shown in FIG. 2(d), the photogenerated charges 208 generated by spectrum 206 are accumulated as the spectrum traverses the CCD integration area, and the charges are transferred to the serial readout register where they are read and digitized. Analyte band 202 forms spectrum 207.

The light signals in FIG. 1 may be generated by fluorescence of the analyte bands by laser induced fluorescence. The TDI mode has several important advantages. Only one row of the CCD is read at a time, reducing the data produced and the readout time up to 516-fold (depending on the spatial binning factor, which is the binning factor in the dimension that is imaging the capillary). Also, a row contains the fluorescence from a single analyte and not from a point on the capillary; the fluorescence is integrated over the entire time the band is in the observation zone. A third advantage is that the fluorescence information from the analyte band can be obtained from a single CCD readout instead of the approximately 4 to 20 readouts required for the snapshot mode. The single readout produces a two- to five-fold reduction in read noise.

Synchronization of Shift Rate. In CZE, the TDI mode is complicated by the fact that the analyte bands move at different rates because of their different electrophoretic mobilities. Hence, the shift rate must be continually decreased during the run to follow different bands. The synchronization of the shift rate to the analyte velocity needs to be accurate to avoid a loss in separation efficiency. Fortunately, such synchronization is not difficult to obtain. The CCD shift rate can be programmed to account for analyte band velocity. For instance, if detection is in a capillary region in which analtye separation is occurring, the photogenerated charge is shifted step-wise from row to row at periodic intervals wherein each interval is longer than the preceding interval by a fixed percentage to account for the slower rate of later bands. Moreover, because both the start time of the CZE run and the distance from the injector to the center of the detection zone are known, the shift time can be determined by the following Formula I:

$$T_{shift} = [(T_{elapsed})(X_{obs})(N_{bin})] / [(N_{ccd})(L_{cap})]$$

where $T_{shift}$ is the time until the next CCD shift, $T_{elapsed}$ is the time since the start of the CZE run, $X_{obs}$ is the length of the observation zone, $N_{bin}$ is the binning factor in the observation (imaging) dimension, $N_{ccd}$ is the number of CCD elements the capillary image illuminates, and $L_{cap}$ is the length of the capillary to the center of the observation zone. The integration times range from 2 to 45 s for a 80 cm capillary, 2 cm observation zone and analyte elution times from 1 to 30 min.

A CCD must shift charge from all rows in concert (i.e., the shift rate is the same for all rows). Because each row receives a signal that originates from a different point in the capillary, the shift rate must be incorrect for all but one specified row. To visualize this concept, consider two analyte bands that are resolved and are in the detection region simultaneously. They must be moving at slightly different velocities because they are resolved; the CCD, which shifts at a single velocity, cannot independently track both. In the experiments described herein, the shift rate was matched to the center of the 2 cm observation zone at the end of an 80 cm capillary, a ±1% difference between the zone velocity at the observation boundaries and TDI shift rate is expected. Thus, in the configuration employed, almost no increase in analyte zone width is expected.

Immediately after injection, the required time between shifts is less than 50 ms. Because the system cannot shift this fast, the tracking of this extremely fast moving (hypothetical) band is not exact. Currently, the system shifts for the maximum 50 ms per spectrum until the calculated shift rate is longer than 50 ms (approximately 2 min.), at which point it shifts at the appropriate rate. Because the shift rate is always decreasing, data are obtained with a nonuniform time resolution, although the spatial resolution remains constant (the system images every band with the same 80 μm resolution). Thus, the early fast bands are sampled faster than later bands. This type of sampling scheme fits well with constant resolution and data acquisition per band. Huang, X.; Coleman, W. F.; Zare, R. N., J. Chromatogr., 1989, 480, 95-110.

A simple method exists to preclude the need for a changing shift rate and thus avoid the potential blurring caused by the TDI method. If the capillary is grounded just prior to the observation zone, the analyte bands would not undergo electrophoresis while being detected, and instead would move at the solution flow velocity. In addition, when separation is accomplished by capillary chromatography instead of electrophoresis, the analyte bands will move at the same velocity once the bands pass the stationary phase of the capillary.

Using the TDI mode, CZE electropherograms with over 700,000 theoretical plates can be obtained. Theoretical plate calculation is based on the full width of a peak at one half of the maximum intensity. With the present invention it is possible to obtain sensitivities for fluorescent tags in the low zeptomole range and differentiate between multiple fluorophores based on different migration times and spectral characteristics.

Description of Axial Illumination. To achieve high sensitivity with the CCD system, longer exposure of the CCD to the analyte fluorescence is advantageous. In most LIF/CZE systems, the laser beam diameter is focused to less than 50 μm and strikes the capillary perpendicular to the separation channel; thus, the analyte is illuminated by the laser for only several milliseconds. In the present system, the capillary is illuminated end-on, and the resultant fluorescence from a 2 cm section is imaged onto the CCD. Fluorescence is collected during the entire residence time of the analyte band in this section.

Problems could occur when axially illuminating a capillary that contains a leading band at high concentration closely followed by other bands. The leading band could absorb a significant fraction of the channeled excitation light, thus reducing the fluorescent signal from later bands also resident in the observation zone. However, such a shadowing effect was not observed at the fluorophore concentrations used in these experiments.

A buffer-filled capillary does not fulfill the requirements of a light-pipe; the index of refraction of the aqueous center is lower than that of the fused silica "cladding." Thus, laser illumination tends to travel in the fused silica wall rather than propagate through the center of the capillary, unless care is taken in the choice of laser-focusing lens and the alignment of the laser beam with respect to the capillary. The focusing lens is chosen to provide a beam waist just smaller than the capillary i.d. This lens provides a large depth of field and hence an extended illumination zone. To facilitate alignment of the laser beam with the capillary, they must be almost exactly parallel to each other. Even with these precautions, significant illumination travels only several centimeters in the capillary channel.

An axially illuminated open tubular liquid chromatography (OTLC) system has been described using capillaries of similar dimensions, but in that case, the solvent was chosen to provide a higher index than the quartz capillary material. Xi, X.; Yeung, E., Anal. Chem., 1990, 62, 1580–1585. For axial illumination of the OTLC system, the laser beam must be propagated through the length of the capillary. In the present case, however, the loss of light after several centimeters is desirable. Many fluorophores, including fluorescein, photodegrade rapidly under moderate-intensity illumination; thus illumination of the analyte band prior to the detection zone is deleterious. For a water-filled fused silica capillary, light radiates from the aqueous channel into the walls as the capillary bends. Thus, just before the 2 cm detection zone, the channel is bent sharply (90 bend over 1 cm). This bending prevents laser light from propagating much past the observation zone and thus greatly reduces photodegradation of the fluorophore before detection. Additionally, the bend in the capillary prevents ambient room light from propagating through the capillary to the detection region.

In conventional systems, when the laser power is high, photodegradation occurs but the fluorescence of the fluorophores is still monitored. In the present system, a 1 cm distance separates the bend in the capillary and the beginning of the observation zone. Thus for 1 cm, or up to 20 s, the fluorescently tagged analyte is subject to laser illumination without the fluorescence being collected. To limit premature photodegradation and a consequent reduction in sensitivity, laser power must be extremely low. The low-intensity illumination and the long observation time are expected to provide the highest signal-to-noise ratios obtainable from a fluorophore susceptible to photodegradation.

An argon ion laser (Model 164, Spectra-Physics, Mountain View, Calif.) provides the laser illumination, and a 488 nm or 514 nm laser-line interference filter (Oriel Corporation, Stratford, Conn.) blocks all but the desired wavelength. For most studies, the laser is operated on the lowest power light-stabilized mode (100 mW), and several neutral density filters are used to reduce the power illuminating the capillary to between 35 and 175 $\mu$W. These illumination levels may be the lowest reported for LIF detection. For all studies except the multiple fluorophore experiment, 488 nm is employed. A 100 mm f.l. fused silica lens (LQP007, Melles Griot, Irvine, Calif.) is used to focus the laser into the 63 $\mu$m i.d. capillary. The capillary alignment is controlled by two linear translation stages and a two-axis tilt stage (Newport Research Corp., Irvine, Calif.) to allow precise alignment with the laser beam.

Figure 4:
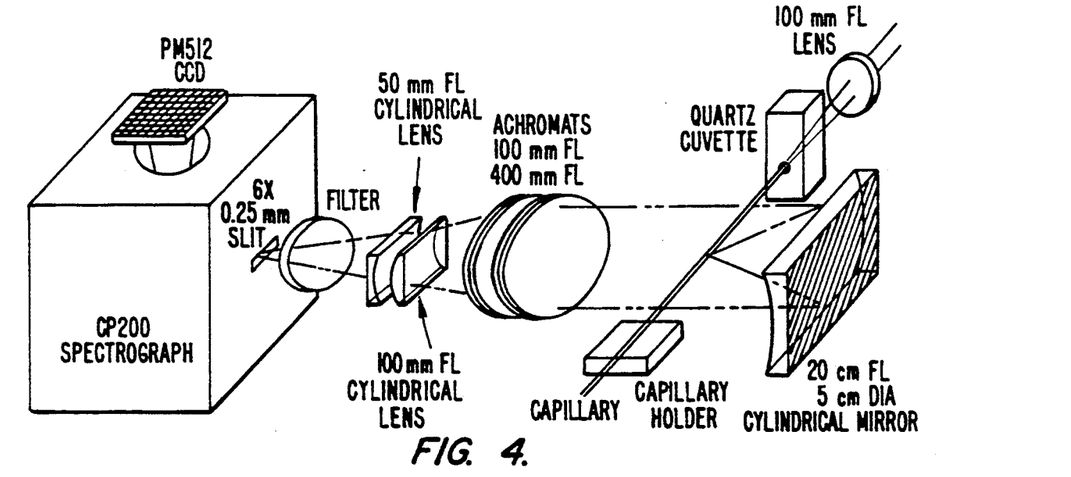
FIG. 4 is schematic of the optical system from FIG. 3, showing the axially illuminated detector.

Detection System. The overall detection system is shown schematically in FIG. 3, and a perspective view of some of the components is illustrated further in FIG. 4. As shown in FIG. 3, the inlet of capillary 301 is positioning in buffer vial 350 that is contained in interlocked plexiglass box 370. The capillary position at 380 is bent at a 90° angle to minimize photodegradation. The capillary is supported by holder 351 and the capillary outlet end is positioned in cuvette 352. As described previously, grounding the capillary just before the detection zone obviates the need to change the shift rate. Grounding can be accomplished by drilling a hole (not shown) by laser into the capillary wall near holder 351 and grounding the capillary thereto. The outlet where detection occurs is held in a lighttight optical enclosure 372. Fitted radiation 353 from laser 354 is focused via lens 355 axially into capillary 301. Mirror 356 reflects the light into the lens. The optics form an image of the capillary on the CCD 302, and a spectrograph 303 disperses the image. Hence, the two dimensions of the CCD array contain different information; one contains the image of the capillary and the other contains wavelength information. For clarity, rows are defined as the dispersive dimension and columns as the capillary image dimension. Thus, the fluorescence from one spot on the capillary (or one analyte band at a particular time) is dispersed along a row of the array. Because the requirements for the optics are different in the two dimensions, cylindrical optics are used.

The optical system consists of five elements. It was designed with the aid of a computer simulation software package entitled "Beam 3 Optical Ray Tracer" (Stellar Software) to maximize the light collection while minimizing aberrations. The first element is a 20 cm f.l. cylindrical mirror 304 (LCP 178, Melles Griot), used instead of a lens to reduce chromatic and spherical aberrations. Next are two achromats shown collectively as 305 (used as the imaging elements) and two cylindrical lenses shown collectively as 306 (LAO 288, LAO 126, LCP155, and LCN129, Melles Griot, respectively). To simplify the alignment of the system, the two cylindrical lenses are held in a single mount, the two achromats are in another mount, and the slit 307 of the spectrograph is fixed. The overall system is designed to form an image of a 2.5 cm by 50 $\mu$m capillary on the 6 by 0.25 mm slit of the spectrograph. This system is F/1 in the wavelength dimension and F/12 in the imaging dimension; both are matched to the F/3 of the spectrograph.

An aberration-corrected imaging spectrograph (CP200, Instruments SA, Edison, N.J.) is used because it maintains a point-to-point relation between the image of the slit and the CCD focal plane. Using the CP200 equipped with a 133 grooves/mm grating 308, the field of view of the CCD is 370 nm; this wavelength window is adjustable from 200 to 1000 nm. The spectral bandwidth is approximately 0.72 nm/CCD element; the resolution is 3.6 nm using a 100 $\mu$m slit and is 9 nm using a 250 $\mu$m slit. As shown, fluorescence emission 309 entering the spectrograph is reflected onto grating 308 by mirror 310.

The detection system consists of a 516 by 516 element CCD (PM512, Photometrics Ltd., Tucson, Ariz.), supplied with the Metachrome II overcoating to extend the wavelength range; the quantum efficiency is more than 10% from less than 200 nm to more than 900 nm, with a maximum of more than 50% at 700 nm. The CCD is controlled with CCD electronics and signal-processing modules (CE200 and CC200, Photometrics Ltd.).

Characteristics that make the PM512 CCD well suited to CZE include its large format, high quantum efficiency, low dark current, and low read noise. In addition, this CCD does not suffer from the charge trapping and poor charge transfer efficiency of some other scientific-grade CCDs. Bredthauer, R. A.; Chandler, C. E.; Janesick, J. R.; McCurnin, I. W.; Sims, G. R., in Instrumentation for Ground-Based Optical Astronomy, L. B. Robinson, Ed.; Springer-Verlag: New York, 1987, p. 468, and Pemberton, J. E.; Sobocinski, R. L.; Sims, G. R., Appl. Spectrosc., 1990, 44, 328–330. With the particular CCD used, the overall system readout noise can be fewer than 6 electrons; at 600 nm, this read noise corresponds to fewer than 12 photons of noise per detector element. The CCD is contained in a liquid-nitrogen-cooled cryostat to reduce the dark current. When the system is operated at $-125°$ C., the measured dark current is less than two electrons per minute per detector element, an insignificant value considering the background luminescence levels found in typical "clean" solvents.

System Control. The system uses a unique set of CCD readout methods. The Photometrics CC200 camera controller is a multibus 68000 computer system with a variety of CCD operations and commands preprogrammed. Several additional commands have been added to the command library using FORTH. The CC200 computer performs all CCD control and executes all high-level commands to the CCD detector. The CC200 computer is controlled with a highspeed IBM AT clone (System 220, Dell Computer Systems) using ASYST version 3.1 (Asyst Software Technologies, Rochester, N.Y.) through a high-speed GPIB interface (PC2A, National Instruments, Austin, Tex.). Considerable effort has gone into designing efficient computer code to optimize data acquisition and system control. The data reduction from two-dimensional spectral and spatial information to electropherogram is performed in real time by data-reduction algorithms in both computers. In addition, the Dell computer controls voltage and monitors voltage, current, and other aspects of system performance; all spectra and electropherograms are stored and displayed using routines written in ASYST.

The CCD detector utilizes the read mode commonly referred to as binning. Sweedler, J. V.; Bilhorn, R. B.; Epperson, P. M.; Sims, G. R.; Denton, M. B., Anal. Chem., 1988, 60, 282A-291A; and Epperson, P. M.; Denton, M. B., Anal. Chem., 1989, 61, 1513-1519. Binning is an electronic method of changing the effective detector element size, using the actual 20 by 20 $\mu$m detector elements as building blocks to make binned elements of any combination desired. Binning is accomplished by combining the photogenerated charge on-chip and then reading out the information in this combined charge packet with a single read. Because the binned information is read using a single readout, the overall read noise is lower than in systems in which the individual detectors are read and their readouts summed in computer memory. With the present system, reading the CCD in the wavelength dimension with fourfold binning produces 128-point spectra. Because of the broad nature of molecular fluorescence spectra in solution, little information is lost using fourfold binning; moreover, both the amount of data generated and the effective read noise are reduced. Binning in the image dimension also reduces the amount of data generated but in this case at a loss of spatial resolution.

As each row of the CCD is read, an entire fluorescence spectrum is acquired. For several applications, observing complete spectra can be useful. For quantitative analysis, we extract the analyte intensity information using the following method. First, a background array is subtracted from each spectrum to remove the electronic offset for each element. Next, the spectrum is multiplied by an array that contains weighing factors for each wavelength. These weighing factors constitute a digital filter that selects the optimum wavelengths for determining the fluorescence intensity. Although sophisticated methods can be used to optimize the extraction of information, these measures were not employed. For the present studies, the weighing factors are set to 1 for the wavelengths of maximum fluorescence intensity, all other weighing factors are zeroed, and the resulting intensity information is summed. For several studies, the resulting electropherograms are digitally smoothed using Blackman's window for the convolution weights and a noise cutoff frequency of 0.33 cycles/point. Blackman, R. B., Tukey, J. W., In The Measurement of Power Spectra; Dover: New York, 1958. This procedure reduces the higher frequency noise but has little effect on the peak width and height.

CZE Apparatus. The CZE portion of the system is similar to that described in previous publications. Gassmann, E.; Kuo, J. E.; Zare, R. N., Science, 1985, 230, 813-814; Pentoney, S. L., Jr.; Huang, X.; Burgi, D. S.; Zare, R. N., Anal. Chem., 1988, 60, 2625-2629; Huang, X., Pang, T.-K.; Gordon, M. J.; Zare, R. N., Anal. Chem., 1987, 59, 2747-2749; and Huang, X.; Gordon, M. J.; Zare, R. N., Anal. Chem., 1988, 60, 1837-1838. A 4 cm section of the polyimide from the 63 $\mu$m i.d., 363 $\mu$m o.d. capillary (Polymicro, Phoenix, Ariz.) is burned off using gentle heating in a flame. Precautions must be taken to avoid damaging the fused silica during this process. After the polyimide is removed, the end of the capillary is carefully scored and broken to leave a surface as flat as possible. Because the laser illumination is directly through the end of the capillary as shown in FIG. 3, any imperfections contribute greatly to scattered light. This end of the capillary is held at ground potential in a modified fluorescence quartz cuvette 352. The incident laser illumination is focused through the cuvette containing the buffer solution and into the capillary. The inlet end of the capillary, held at high positive voltage, is placed in a 4 mL vial 350 containing approximately 2-3 mL of electrolyte buffer solution. The electrical circuit completion is made by strips of Pt foil submersed in each buffer reservoir. All separations employ a 20 kV potential across the capillary. The current through the system is measured by monitoring the voltage drop across a 10 k$\Omega$ resister at the ground side of the capillary.

All samples are introduced using gravity injection in which the inlet of the capillary is removed from the buffer vial and placed in an elevated sample vial. This injection method is chosen to avoid the sampling bias associated with electrokinetic injection. For these experiments, the height displacement is 5 cm and the injection time is from 10 to 30 s, which introduces from 4 to 13 nL of sample. To prevent sample carryover from an injection, the inlet was dipped into a vial of water after each injection. In addition, the polyimide was removed from the first 5 mm of the capillary.

Regents. Water used to prepare solutions is freshly purified (Ion-X Adsorber and Research Deionizer, Cole Parmer, Chicago, Ill.; LD2A Demineralizer and Mega-Pure Still, Corning Glassworks, Corning, N.Y.). The supporting electrolyte for all the experiments is 50 mm borate (pH 9.0) prepared from reagent-grade sodium borate decahydrate and boric acid (Mallincrokdt). Stock solutions of fluorescein (Sigma), sulforhodamine 101 (Exciton), and fluorescein isothiocyanate (FITC) isomer I (Aldrich) are prepared at approximately $10^{-5}$ M and used without further purification. All low-concentration solutions are made daily by serial dilutions from these stock solutions. All amino acids are purchased from Sigma and used without further purification. Reagent grade sodium bicarbonate (Sigma) and acetone (Baker) are used in the derivitization reactions described below.

Derivitization. Amino acids are derivitized with FITC isomer I in a modified version of the procedure described earlier. Kawauchi, H.; Tuzimura, K.; Maeda, H.; Ishida, N., J. Biochem., 1969, 66, 783–789. Briefly, individual solutions of amino acids are prepared at approximately 100 mm in 200 mm NaHCO$_3$ (pH 9.0). Approximately 10 mm FITC is dissolved in a 95% acetone, 5% water solution that contains 0.001% pyridine (by volume) to catalyze the reaction. Derivitization is initiated by the addition of 100 μL FITC solution to 500 μL amino acid solution. The reaction is carried out in the dark at 20° C. for approximately 8 h. FITC-amino acid solutions are maintained separately in opaque vessels at 4° C. for up to two days and are mixed immediately prior to separation.

RESULTS

Figure 5A:
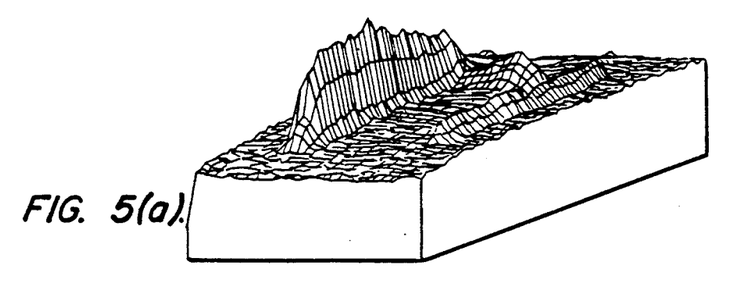
FIGS. 5(a), 5(b), and 5(c) are snapshots taken in succession (0.5 s exposures) of the focal plan output for a 4 nL injection of $8 \times 10^{-10}$ M FITC.
Figure 5B:
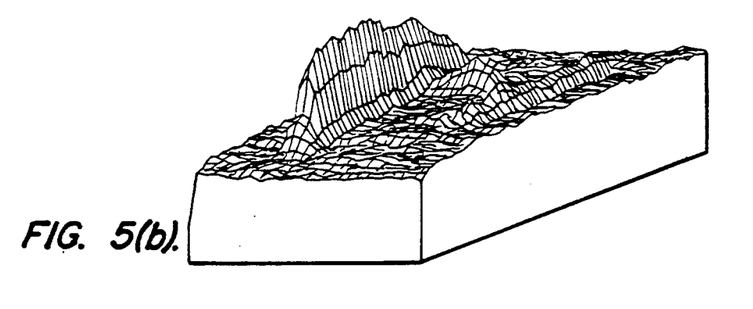
Figure 5C:
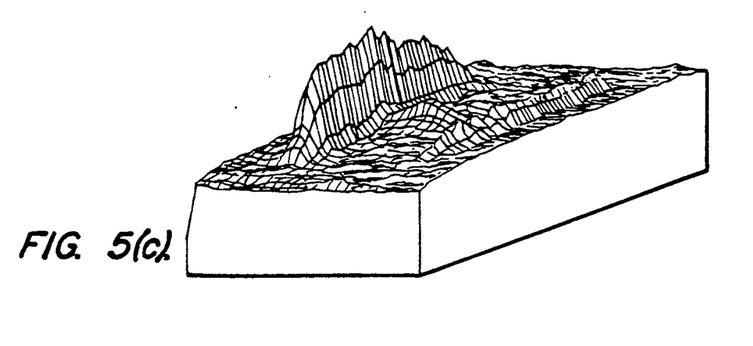

System Performance. FIGS. 5(a), 5(b), and 5(c) illustrate the ability of the optical system to image the capillary accurately and of the CCD/LIF system to measure the fluorescence from an analyte undergoing electrophoresis. These Figures show the focal plane output of the CCD for a single 4 nL injection of $8 \times 10^{-10}$ M FITC The CCD is used in the conventional snapshot mode, in which a shutter is placed between the capillary and the spectrograph slit to time the exposure of the CCD. After the shutter is closed, the CCD is read. FIG. 5(a) is a 0.5 s exposure taken after approximately 13 minutes, FIG. 5(b) is taken 4 s later, and FIG. 5(c), 6 s after FIG. 5(b). The data in these Figures show the CCD output corresponding to approximately 460 to 600 nm, less than 50% of the spectral information stored in the CCD. To reduce the data further, the CCD is read with 4 by 4 binning, the resulting data are smoothed in the wavelength dimension, and every second wavelength point and every second spatial line is plotted. This procedure reduces the focal plane output from 250,000 detector elements to the approximately 2000 points plotted. With 4 by 4 binning, each element corresponds to an 80 by 80 μm area on the detector focal plane and a 320 μm length of capillary. Both the Rayleigh line and the strongest Raman line are clearly visible along with the fluorescence from FITC. Comparison of these images shows the motion of the FITC band.

Figure 6A:
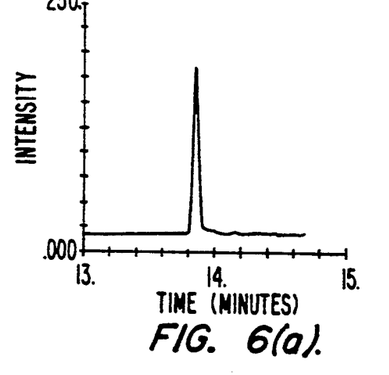
FIGS. 6(a), 6(b), and 6(c) are electropherograms illustrating the effect of changing the TDI shift rate on electrophoretic efficiency for a series of 3 amol fluorescein isothiocyanate FITC injections.
Figure 6B:
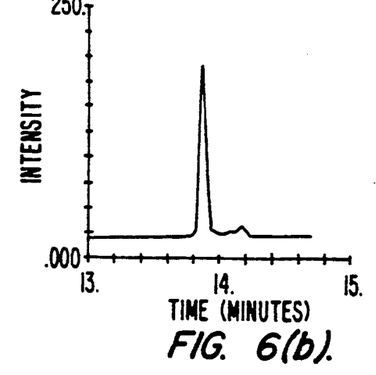
Figure 6C:
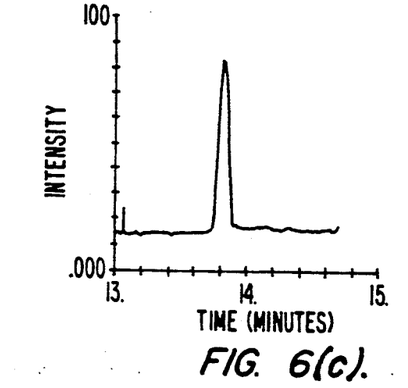

FIGS. 6(a), 6(b), and 6(c) illustrate the ability of the TDI mode to track an analyte. These electropherograms show a series of 4 nL injections of $8 \times 10^{10}$ M FITC for a variety of shift rates. In FIG. 6(a), the shift rate is that calculated using Formula I; electropherograms in FIGS. 6(b) and 6(c) are obtained using 10% faster and 20% slower shift rates, respectively. For the optimum shift rate, the efficiency (N) is 400,000 theoretical plates, but as the shift rate is changed, N decreases; however, with a 10% error in shift rate, efficiencies of 250,000 theoretical plates are obtained. Thus, extremely accurate estimations of shift rate are not required.

Multiple Fluorophores. To determine the flexibility of the system to detect multiple fluorophores, a mixture of two commonly used derivitizing agents was analyzed. Two changes in the detection system are made for this experiment: the laser illumination is changed to 514 nm, and a 525 nm cutoff filter is inserted before the spectrograph slit to reduce the Rayleigh scattering. FIG. 7 shows the TDI electropherogram of $3 \times 10^{-9}$ M sulforhodamine 101 and $9 \times 10^{-9}$ M fluorescein. The CCD is binned fourfold in the wavelength dimension, and the resulting 128-point spectra is stored. To aid visualization of the data, the CCD is read using sixteen-fold binning in the image dimension, thus reducing the number of spectra from more than 25,000 to less than 2000. Every fourth spectrum collected between 9 and 14 minutes is plotted in FIG. 7. The spectra shown in this Figure are plotted with equal spacing; because of the nonlinear data-acquisition rate, the time axis is nonlinear.

FIG. 7 shows the spectra of the fluorophores, as well as the 514 nm scattered light and two Raman bands from water. The fluorescence emission of the sulforhodamine is to the red of the emission from fluorescein. This Figure also illustrates another effect of the changing shift rate; because the data acquisition rate is continually slowing down, the background (i.e., Rayleigh and Raman bands) is continually increasing in intensity. This effect does not alter the sensitivity or utility of this technique. If desired, however, each spectrum can be divided by its integration time. The ability to detect and differentiate multiple fluorophores is important to several applications, notably in DNA sequencing when identifying each of the four bases. Intensity information for fluorescein can be extracted from FIG. 7 by summing the intensities from approximately 530 to approximately 580 nm.

Figure 8A:
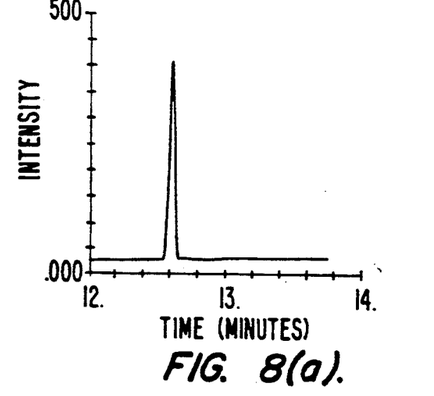
FIGS. 8(a), 8(b), 8(c), and 8(d) are TDI electropherograms of FITC at different concentrations.
Figure 8B:
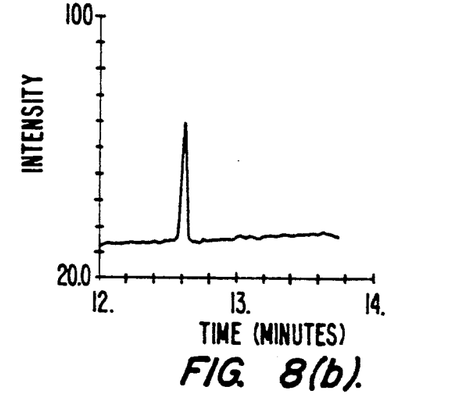
Figure 8C:
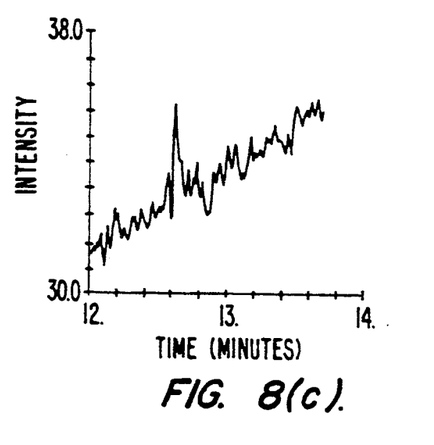
Figure 8D:
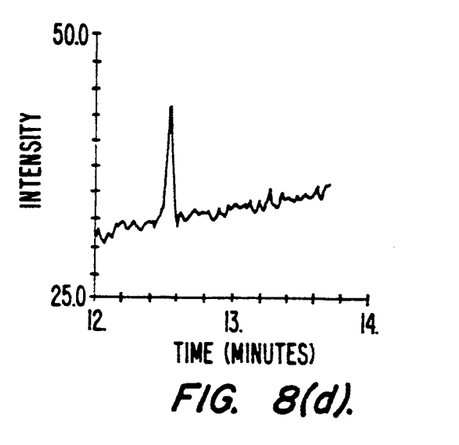

Sensitivity. FIGS. 8(a), 8(b), 8(c), and 8(d) illustrate the sensitivity of the system with a series of electropherograms of FITC. FIGS. 8(a), 8(b), and 8(c) represent 4 nL injections of $7 \times 10^{-10}$ M, $6 \times 10^{-11}$ M, and $6 \times 10^{-12}$ M solutions, whereas FIG. 8(d) represents a 13 nL injection of a $6 \times 10^{-12}$ M solution. The limit of detection (LOD) for a 4 nL injection is $3 \times 10^{-12}$ M, or 12 zmol, calculated using two times the peak-to-peak baseline noise. The peak in FIG. 8(c) represents approximately 14,000 FITC molecules. Increasing the injection to 13 nL does not improve the mass detection limit but improves the LOD concentration to $1 \times 10^{-12}$ M while retaining good efficiency. An alternative method of calculating baseline noise improves the LODs by a factor of 2. Cheng. Y.-F; Dovichi, N. J.; Science, 1988, 242, 562–564.

Figure 9:
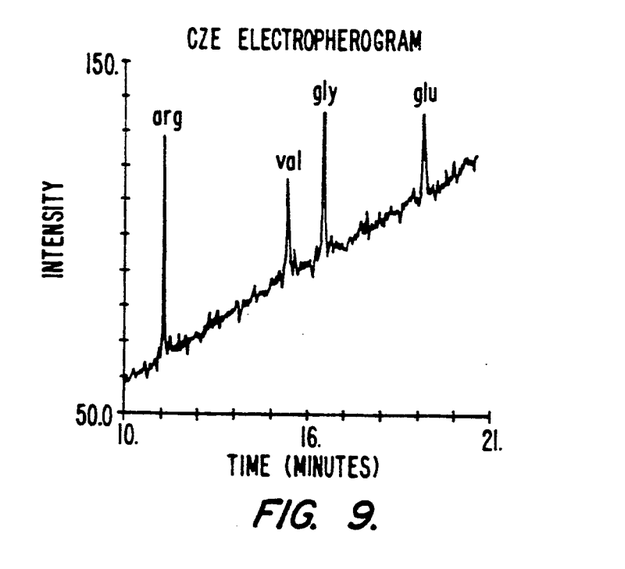
FIG. 9 is a TDI electropherogram of four FITC-amino acids, with the concentration of injected FITC-arginine, FITC-valine, and FITC-glycine at $7 \times 10^{-11}$ M, and FITC-glutamate at $8 \times 10^{-11}$ M.

FIG. 9 shows an electropherogram of four FITC-amino acids: arginine, valine, and glycine at $7 \times 10^{-11}$ M, and glutamate at $8 \times 10^{-11}$ M. The injection volume is 13 nL. The LODs for the FITC-amino acids are in the 20 to 80 zmol range, which compares favorably to the best previous work.

It is to be understood that while the invention has been described above in conjunction with preferred specific embodiments, the description and examples are intended to illustrate and not limit the scope of the invention, which is defined by the scope of the appended claims.

What is claimed is:

1. An apparatus for detecting analytes in a sample, comprising:
   means for separating said sample into migrating analyte bands migrating along a direction, said separation means comprising a capillary tube with an inlet and outlet in which a detection zone is located in the capillary tube, and means for applying a voltage across a portion of the tube;
   means for generating radiation signals to indicate the presence of an analyte band in the detection zone;
   an array of solid state detectors capable of collecting the radiation signals to produce charges, wherein the array is aligned with the detection zone in a sequence in the direction of the migrating analyte bands, so that when a migrating analyte band is in the detection zone the radiation signals indicative of said band are directed to each of the detectors in sequence as the band migrates across the detection zone, said array having an output;

means for shifting the charges from each detector to the respective adjacent detector in the direction of the migration at a shift rate that is synchronized to the movement of the band such that the charges corresponding to the radiation signals of an analyte band can be accumulated at the array output; and readout means to read the accumulated charges from the array output.

2. The apparatus as defined in claim 1 further comprising means for transmitting said radiation signals to the array of solid state detectors, wherein each detector comprises a linear row of detector elements that is arranged transverse to the direction of migration, and wherein the transmitting means is such that radiation signals transmitted to one detector element of a row are at different wavelengths from those of radiation signals transmitted to another detector element that is located on said row.

3. The detection apparatus as defined in claim 2 wherein the means for generating radiation signals comprises a laser wherein radiation from the laser is directed axially into the capillary.

4. The detection apparatus as defined in claim 3 wherein the capillary is bent at a location adjacent to and downstream from the detection zone so that radiation from the laser does not illuminate the analyte bands until just before they reach the detection zone.

5. The detection apparatus as defined in claim 4 wherein the shift rate is continually decreasing.

6. The detection apparatus as defined in claim 5 wherein the charges are shifted step-wise from detector to detector at periodic intervals wherein each interval is longer than the preceding interval by a fixed percentage.

7. The detection apparatus as defined in claim 4 further comprising means for grounding the capillary at a location adjacent to and upstream from the detection zone so that the analyte bands move substantially at a constant speed in the detection zone.

8. An apparatus for detecting analytes in a sample, comprising:

means for separating said sample into migrating analyte bands migrating along a direction comprising a capillary tube with a stationary phase wherein separation is accomplished by chemical interaction between the stationary phase and the analytes;

means for generating radiation signals to indicate the presence of an analyte band in a detection zone;

an array of solid state detectors capable of collecting the radiation signals to produce charges, wherein the array is aligned with the detection zone in a sequence in the direction of the migrating analyte bands, so that when a migrating analyte band is in the detection zone the radiation signals indicative of said band are directed to each of the detectors in sequence as the band migrates across the detection zone, said array having an output;

means for shifting the charges from each detector to the respective adjacent detector in the direction of the migration at a shift rate that is synchronized to the movement of the band such that the charges corresponding to the radiation signals of an analyte band can be accumulated at the array output; and readout means to read the accumulated charges from the array output.

9. The detection apparatus as defined in claim 8 further comprising means for transmitting said radiation signals to the array of solid state detectors, wherein each detector comprises a linear row of detector elements that is arranged transverse to the direction of migration, and wherein the transmitting means is such that radiation signals transmitted to one detector element of a row are at different wavelengths from those of radiation signals transmitted to another detector element that is located on said row.

10. The detection apparatus as defined in claim 9 wherein the means for generating radiation signals comprises a laser wherein radiation from the laser is directed axially into the capillary.

11. The detection apparatus as defined in claim 10 wherein the capillary is bent at a location adjacent to and downstream from the detection zone so that radiation from the laser does not illuminate the analyte bands until just before they reach the detection zone.

12. The detection apparatus as defined in claim 11 wherein the shift rate is continually decreasing.

13. The detection apparatus as defined in claim 12 wherein the charges are shifted step-wise from detector to detector at periodic intervals wherein each interval is longer that the preceding interval by a fixed percentage.

14. The detection apparatus as defined in claim 11 further comprising means for grounding the capillary at a location adjacent to and upstream from the detection zone so that the analyte bands move substantially at a constant speed in the detection zone.

15. An apparatus for detecting analytes in a sample, comprising:

means for separating said sample into migrating analyte bands migrating along a direction in a detection zone;

means for generating radiation signals to indicate the presence of an analyte band in the detection zone;

means for transmitting said radiation signals to an array of solid state detectors capable of collecting the radiation signals to produce charges, wherein the array is aligned with the detection zone in a sequence in the direction of the migrating analyte bands, so that when a migrating analyte band is in the detection zone the radiation signals indicative of said band are directed to each of the detectors in sequence as the band migrates across the detection zone, said array having an output, wherein each detector comprises a linear row of detector elements that is arranged transverse to the direction of migration, and wherein the transmitting means is such that radiation signals transmitted to one detector element of a row are at different wavelengths from those of radiation signals transmitted to another detector element that is located on said row;

means for shifting the charges from each detector to the respective adjacent detector in the direction of the migration at a shift rate that is synchronized to the movement of the band such that the charges corresponding to the radiation signals of an analyte band can be accumulated at the array output; and readout means to read the accumulated charges from the array output.

16. The detection apparatus as defined in claim 15 wherein the sample is separated in a capillary and wherein the means for generating radiation signals comprises a laser wherein radiation from the laser is directed axially into the capillary.

17. The detection apparatus as defined in claim 16 wherein the capillary is bent at a location adjacent to and downstream from the detection zone so that radiation from the laser does not illuminate the analyte bands until just before they each the detection zone.

18. The detection apparatus as defined in claim 17 wherein the means for separating said sample comprises a capillary tube with an inlet and outlet and in which a detection zone is located in the capillary tube, and means for applying a voltage across a portion of the tube.

19. The detection apparatus as defined in claim 18 wherein the shift rate is continually decreasing.

20. The detection apparatus as defined in claim 19 wherein the charges are shifted step-wise from detector to detector at periodic intervals wherein each interval is longer than the preceding interval by a fixed percentage.

21. The detection apparatus as defined in claim 18 further comprising means for grounding the capillary at a location adjacent to and upstream from the detection zone so that the analyte bands move substantially at a constant speed in the detection zone.

22. A time-delayed integration method for detecting analyte bands from a sample, comprising the steps of:
separating said sample into migrating analyte bands along a direction;
generating radiation signals that indicate the presence of the analyte bands as they move through the detection zone;
transmitting said radiation signals to an array of solid state detectors capable of collecting the radiation signals to produce charges, wherein the array is aligned with the detection zone in a sequence in the direction of the migrating analyte bands, wherein the detectors are arranged so that when a migrating analyte band is in the detection zone the radiation signals indicative of said band is directed to each of the detectors in sequence as the band migrates across the detection zone, wherein said detector comprises a linear row of detector elements that is arranged transverse to the direction of migration, and wherein said signals are transmitted such that radiation signals transmitted to one detector element in a row of detector elements are at different wavelengths from those of radiation signals transmitted to another detector element that is located on said row;
accumulating the charge by shifting said charge, one detector at a time, beginning from a first detector sequentially toward an array output wherein the shifting is at a specific rate that is synchronized to the movement of the migrating analyte bands; and
reading the accumulated charge from the device output.

23. The time-delayed integration method as defined in claim 22 wherein the sample is separated in a capillary and wherein the step of generating radiation signals comprises directing laser radiation axially into the capillary and onto the analyte bands.

24. The time-delayed integration method as defined in claim 23 wherein the step of separating said sample comprises:

placing the sample in the capillary which has an inlet and outlet and wherein the detection zone is located in the capillary tube; and
applying a voltage across a portion of the tube.

25. The time-delayed integration method as defined in claim 24 wherein the step of accumulating the charge comprises continually decreasing the shift rate.

26. The time-delayed integration method as defined in claim 25 wherein the charges are shifted step-wise from row to row at periodic intervals wherein each interval is longer than the preceding interval by a fixed percentage.

27. The time-delayed integration method as defined in claim 24 further comprising the step of grounding the capillary at a location adjacent to and upstream from the detection zone just before the analyte bands reach the detection zone so that the analyte bands move substantially at a constant speed in the detection zone.

28. The time-delayed integration method as defined in claim 23 wherein the step of separating said sample comprises:
placing the sample in the capillary which has a stationary phase wherein the analyte bands are differentiated by chemical interactions with the stationary phase.

29. The time-delayed integration method as defined in claim 28 wherein the step of accumulating the charge comprises continually decreasing the shift rate.

30. The time-delayed integration method as defined in claim 29 wherein the charges are shifted step-wise from row to row at periodic intervals wherein each interval is longer than the preceding interval by a fixed percentage.

31. The time-delayed integration method as defined in claim 28 further comprising the step of grounding the capillary at a location adjacent to and upstream from the detection zone just before the analyte bands reach the detection zone so that the analyte bands move substantially at a constant speed in the detection zone.

32. The time-delayed integration method as defined in claim 22 wherein the sample is separated in a capillary, wherein the step of generating radiation signals comprises directing laser radiation axially into the capillary and wherein the capillary is bent at a location near and downstream from the detection zone so that radiation from the laser does not illuminate an analyte band until just before said band reaches the detection zone.

33. The time-delay integration method of claim 32 wherein the step of separating said sample comprises:
placing the sample in the capillary which has an inlet and outlet and wherein the detection zone is located in the capillary; and
applying a voltage across the inlet and outlet.

34. The time-delayed integration method as defined in claim 33 wherein the step of accumulating the charge comprises continually decreasing the shift rate.

35. The time-delayed integration method as defined in claim 34 wherein the charges are shifted step-wise from row to row at periodic intervals wherein each interval is longer than the preceding interval by a fixed percentage.

36. The time-delayed integration method as defined in claim 33 further comprising the step of grounding the capillary at a location adjacent to and upstream from the detection zone just before the analyte bands reach the detection zone so that the analyte bands move substantially at a constant speed in the detection zone.

37. The time-delayed integration method as defined in claim 32 wherein the step of separating said sample comprises:

placing the sample in the capillary which has a stationary phase wherein the analyte bands are differentiated by chemical interactions with the stationary phase.

38. The time-delayed integration method as defined in claim 37 wherein the step of accumulating the charge comprises continually decreasing the shift rate.

39. The time-delayed integration method as defined in claim 38 wherein the charges are shifted step-wise from row to row at periodic intervals wherein each interval is longer than the preceding interval by a fixed percentage.

40. The time-delayed integration method as defined in claim 37 further comprising the step of grounding the capillary at a location adjacent to and upstream from the detection zone just before the analyte bands reach the detection zone so that the analyte bands move substantially at a constant speed in the detection zone.

* * * * *

UNITED STATES PATENT AND TRADEMARK OFFICE
CERTIFICATE OF CORRECTION

PATENT NO. : 5,141,609
DATED : AUGUST 25, 1992
INVENTOR(S) : Sweedler et al.

It is certified that error appears in the above-identified patent and that said Letters Patent is hereby corrected as shown below:

Column 16, line 29 in Claim 13:     replace "that" with --than--

Column 17, line 8 in Claim 17:      replace "each" with --reach--

Column 17, line 42 in Claim 22:     replace "is" with --are--

Column 17, line 44 in Claim 22:     replace "said" with --each--

Column 18, line 49 in Claim 33:     replace "time-delay" with --time-delayed--

Signed and Sealed this

Seventh Day of December, 1993

Attest:

BRUCE LEHMAN

Attesting Officer

Commissioner of Patents and Trademarks